US012685829B2

(12) United States Patent
Kern

(10) Patent No.: US 12,685,829 B2
(45) Date of Patent: Jul. 21, 2026

(54) AEROSOL GENERATOR HAVING A SANDWICH CONSTRUCTION

(71) Applicant: NEBU-TEC MED. PRODUKTE EIKE KERN GMBH, Elsenfeld (DE)

(72) Inventor: Joachim Kern, Elsenfeld (DE)

(73) Assignee: NEBU-TEC MED. PRODUKTE EIKE KERN GMBH, Elsenfeld (DE)

( * ) Notice: Subject to any disclaimer, the term of this patent is extended or adjusted under 35 U.S.C. 154(b) by 855 days.

(21) Appl. No.: 18/008,362

(22) PCT Filed: Jun. 8, 2020

(86) PCT No.: PCT/DE2020/100481
§ 371 (c)(1),
(2) Date: Dec. 5, 2022

(87) PCT Pub. No.: WO2021/249585
PCT Pub. Date: Dec. 16, 2021

(65) Prior Publication Data
US 2023/0302232 A1 Sep. 28, 2023

(51) Int. Cl.
*A61M 11/00* (2006.01)
*A61M 15/00* (2006.01)
*B05B 17/00* (2006.01)

(52) U.S. Cl.
CPC ...... *A61M 11/005* (2013.01); *A61M 15/0085* (2013.01); *B05B 17/0646* (2013.01); *A61M 2205/0294* (2013.01); *A61M 2207/10* (2013.01)

(58) Field of Classification Search
CPC ............ A61M 11/005; A61M 15/0085; A61M 220/0294; A61M 2207/10; A61M 2207/00; B05B 17/0646
See application file for complete search history.

(56) References Cited

U.S. PATENT DOCUMENTS

2003/0192956 A1 10/2003 Varanasi et al.
2010/0213274 A1* 8/2010 Yu ........................ B05B 17/0646
239/102.2
(Continued)

FOREIGN PATENT DOCUMENTS

DE 202009008436 U1 9/2009
WO 2021249585 A1 12/2021

OTHER PUBLICATIONS

Written Opinion dated Feb. 18, 2021 from corresponding International Application No. PCT/DE2020/100481, filed Jun. 8, 2020.
(Continued)

*Primary Examiner* — Vishal Pancholi
(74) *Attorney, Agent, or Firm* — Brian D. Kaul; Westman, Champlin & Koehler, P.A.

(57) ABSTRACT

An aerosol generator includes a carrier structure having an opening, a mesh membrane covering the opening and overlaying an upper surface of the carrier structure, and a closing ring arranged on an upper surface of the mesh membrane that faces away from the carrier structure. The mesh membrane includes at least two gluing openings extending through the mesh membrane and distributed evenly around a circumference of the mesh membrane. Cured adhesive columns protrude through the gluing openings and mechanically connect an adhesive layer located below the mesh membrane that is bonded to the upper surface of the carrier structure to an adhesive layer located above the mesh membrane that is bonded to a lower surface of the closing ring. The adhesive columns mechanically connect the mesh membrane to the carrier structure and the closing ring.

12 Claims, 1 Drawing Sheet

(56) References Cited

U.S. PATENT DOCUMENTS

| | | |
|---|---|---|
| 2011/0233302 A1 | 9/2011 | Lin et al. |
| 2012/0172739 A1* | 7/2012 | Kern .................... F16K 15/148 |
| | | 128/205.24 |

OTHER PUBLICATIONS

International Search Report dated Feb. 18, 2021 from corresponding International Application No. PCT/DE2020/100481, filed Jun. 8, 2020.

* cited by examiner

AEROSOL GENERATOR HAVING A SANDWICH CONSTRUCTION

CROSS-REFERENCE TO RELATED APPLICATIONS

This Application is a Section 371 National Stage Application of International Application No. PCT/DE2020/100481, filed Jun. 8, 2020 and published as WO 2021/249585 A1 on Dec. 16, 2021, not in English.

FIELD

The present invention relates to an aerosol generator according to the preamble of claim 1 as well as a method for its manufacture.

BACKGROUND

Nebulizers are used to aerosolize fluids, i.e. convert a larger, cohesive volume of fluid into a mist of more or less fine fluid droplets. They are used in particular in the therapy of respiratory and lung diseases, the fluid to be aerosolized for this purpose usually being an aqueous active substance solution. The desired size distribution of the aerosol droplets depends on the desired deposition site. A treatment of bronchial diseases requires droplet sizes of 5 microns and more, whereas if the active substance is to be deposited in the pulmonary alveoli, the droplet sizes should be below 5 microns if possible.

The heart of a nebulizer, which serves to nebulize or aerosolize the fluid, is the actual aerosol generator. Today, aerosol generators of the mesh membrane type are widely used for this purpose. In this type of aerosol generator, the mesh membrane, a small plate with a round outline, which is perforated in a central area and is usually curved like a spherical cap, is attached to a carrier disk which is set in rapid vibration by a piezo ceramic. As a result, the fluid lying on one side of the mesh membrane is pressed into the pores of the perforation and discharged on the opposite outlet side as an aerosol, i. e. as a more or less fine mist of fluid droplets. The aerosol generator is held in its working position inside the nebulizer casing by being clamped between two approximately toroidal rubber rings or lips made of as soft a rubber as possible.

Parameters that influence the droplet size distribution are the diameter and geometry of the pores, the vibration frequency, which is determined by the frequency of the applied voltage, the Shore hardness and the points of contact with the rubber rings or lips pinching the aerosol generator, as well as the three-dimensional shape of the standing vibration of the mesh membrane resulting from the geometry and structure of the aerosol generator. In the case of the latter, it is important whether the piezo ceramic is connected to the mesh membrane directly or only indirectly via an intermediate element, what thickness and shape the mesh membrane has and how the membrane is connected to the piezo ceramic or to the intermediate element respectively.

The geometry of the mesh membrane is also of great influence. In the state-of-the-art, mesh membranes with a round outline and a dome-like, convex curvature in the perforated area have prevailed.

In the case of aerosol generators that are used today of the described mesh membrane-type, the usual structure is, that on the upper side of a disc made of (stainless) steel, which is annular in shape and therefore has a concentric, continuous opening, the mesh membrane is attached, while the stimulating piezo ceramic, also of annular shape, is attached to the opposite underside of the disc. In the state-of-the-art, the attachment is preferably carried out by gluing the components together using an adhesive approved for medical purposes. Such an adhesive must not release any harmful substances into any aqueous active substance solution with which it comes into contact.

In order to be able to glue them with such compatible adhesives, the mesh membrane must be made of an appropriate material. In the state-of-the-art, small stainless steel plates are therefore usually used as mesh membranes, since these can be glued both to stainless steel intermediate discs and directly to the ceramic.

The disadvantage of mesh membranes made of stainless steel, however, is their comparatively complex and therefore expensive production.

Electro-galvanic production, in which mesh membranes of the desired shape, including the perforation, are electro-galvanically deposited in a correspondingly shaped negative, would be significantly cheaper because it can be easily parallelized. This allows large quantities to be produced quickly and easily. However, this method is not compatible with the use of stainless steel or other metal alloys. In contrast, the material of choice for electrogalvanic production is nickel.

Another interesting material class for mesh membranes in the future are plastics, in particular a fluorine-terminated plastics. These offer the advantage that they have a hydrophobic surface, which means that they are less easily wetted by the water-based active ingredient solutions usually used, which is conducive to the formation of finer droplets and reduces adhesion and thereby counteracts accumulation of fluid, which has left the pores without sufficient kinetic energy, on the outlet side, something that is difficult to avoid in case of metal mesh membranes.

Mesh membranes made of nickel, as well as of fluorine-terminated plastic have in common, however, that they cannot be glued to the carrier disc of the aerosol generator, or at least not by means of an adhesive approved for contact with active ingredient liquids. So far, this has prevented their use in aerosol generators, which, as explained, is definitely desirable.

The published application US 2011/0233302 A1 proposes an aerosol generator with a mesh membrane and a driving element adhesively bonded to a top surface thereof, wherein the mesh membrane features a central nebulization region with nozzles and a radially further outwardly lying bonding region with bonding holes. When an adhesive layer is applied on the bonding region, the adhesive flows into the bonding holes, which, after curing, enables a very firm connection between the dried adhesive layer and the mesh membrane.

Regarding the size and shape of the bonding holes in absolute regard and/or relative to the size of the nozzles the document does not make any specific statements, however in the figures it discloses bonding holes of the same magnitude and (circular) shape as the nozzles.

The utility model specification DE 20 2009 008 436 U1 discloses a device for producing droplets comprising a nozzle disc, which is sandwiched in between a bonding plate and a vibration plate, both of which are circular, and fixed by means of adhesive bonding. To improve the adhesive bond, the nozzle disc has in its edge region circle-segment shaped continuous openings, by means of which layers of adhesive on either side of the nozzle disc can come into contact and bond. In particular four symmetrically arranged continuous openings are proposed.

SUMMARY

Against this background, the present invention has set itself the task of enabling the generation of finer aerosol droplets with aerosol generators having mesh membranes that are difficult or impossible to adhesively bond.

This object is solved in an elegant way by an aerosol generator according to claim 1, which can be manufactured according to claim 10.

In the aerosol generator according to the invention, the mesh membrane is securely fastened without it itself being glued, by means of inserting continuous openings, referred to here as gluing openings, extending from the top surface to the bottom surface around the outer edge of the membrane. In the finished aerosol generator, column-like structures made of cured adhesive protrude through these gluing openings and connect layers of adhesive located above and below the membrane. The two layers of adhesive are respectively bonded to a carrier structure or disc located below the mesh membrane or to a closing ring located above the mesh membrane. This keeps the membrane tight and immobile without it being bonded itself. Of course, this structure could also be used with a mesh membrane made of adhesively bondable material.

Such an aerosol generator according to the invention is produced from the provided components, mesh membrane, closing ring and the support structure with opening comprising the piezo ceramic, in such a way that initially the mesh membrane, which usually has a circular outline, has a desired number of gluing openings introduced in a desired pattern along its outer edge, for example by drilling. Alternatively and preferably, the mesh membrane would already be manufactured in the desired configuration. Furthermore, a highly viscous but still sufficiently free-flowing adhesive is applied to the upper side of the carrier structure, for example as a ring-shaped formation enclosing the opening. This adhesive formation or adhesive ring should have a volume that corresponds to the total volume of all gluing openings in the mesh membrane (although when determining the volume of an gluing opening, one has to imagine the top and bottom as being closed by flat surfaces) plus an amount that is sufficient to form two layers of adhesive of a desired thickness between the membrane and the support structure or the membrane and the closing ring.

Then the mesh membrane is placed on the carrier structure in such a way that the opening of the carrier structure is covered in the desired way, in particular concentrically to the usually round opening, and it is pressed on so far that adhesive penetrates into the gluing openings and is pressed through them so that an even adhesive layer of the desired thickness is formed between the carrier structure and the mesh membrane. As stated above, the amount of adhesive is measured in such a way that the volume of adhesive not only completely fills the gluing openings of the mesh membrane, but also comes out at the top and forms adhesive spots protruding over the upper side of the mesh membrane. The annular closing ring is now placed on this upper side and pressed on firmly enough to form an adhesive layer of the desired thickness that is as uniform as possible, with any excess adhesive spilling out over the edge of the ring. This is preferably removed in order to avoid negatively influencing the vibration properties of the membrane. The removal is done either directly, i.e. while the adhesive is still liquid, or, to avoid the risk of unwanted displacement of the components, in a post-treatment step after curing.

The type of attachment according to the invention by means of the described sandwich-like structure made up of carrier structure-mesh membrane-closing ring with an adhesive layer in between can also be used in an aerosol generator with a mesh membrane made of material that cannot be bonded or is difficult to bond. This would either reduce the production costs of the aerosol generator, for example when using an electrogalvanically produced mesh membrane made of nickel, and/or the droplet size distribution would be positively influenced, for example when using a mesh membrane made of plastic, in particular fluorine-terminated plastic.

A further advantage of the type of attachment according to the invention has been found to be that even with nickel membranes, a small average droplet size and a distribution of the droplet sizes that is more penetrative to the lungs are achieved. In experiments, droplet size distributions were measured in which more than 80% of the mass of the aerosol was present in droplets with a diameter of less than 5 micrometers. This represented a significant increase compared to similarly shaped stainless steel mesh membranes, which were attached in the conventional way by direct gluing to the support structure.

So far, it has not been fully clarified how the attachment can exert this positive influence. However, it can be speculated that the introduction of force through a series of discrete points, namely through the adhesive columns penetrating the bonding openings, which are evenly distributed over the circumference of the mesh membrane, possibly a more uniform and symmetrical shape of the standing spatial waveform of the mesh membrane than is the case with adhesive bonding across the entire surface.

Further advantageous embodiments of the present invention are presented below, which can be combined with one another in a suitable form, provided they are not obviously mutually exclusive.

Although the field of application of the present invention is not limited to this, the mesh membrane used in the aerosol generator according to the invention is preferably made of a material which cannot be bonded or only insufficiently by means of an adhesive approved for medical purposes, in particular contact with active substance liquids. A mesh membrane made of nickel or a plastic, in particular a plastic containing fluorine-carbon compounds, is particularly preferably used.

The gluing openings of the mesh membrane according to the invention are preferably arranged in multiples and/or uniformly and/or all or in groups at the same distance from the edge of the mesh membrane. The gluing openings are particularly preferably arranged in one or two rings arranged concentrically around a center point of the mesh membrane, with each of the rings having three or more equally distributed gluing openings. The bonding openings are preferably round or square with a radius or an edge length of between 0.1 and 1 millimeter and are at a distance from the outer edge of the mesh membrane which is at least one and a half times its radius or half its edge length.

In one embodiment of the present invention, the carrier structure of the aerosol generator according to the invention is a round steel disc with a concentric, continuous opening in the middle, with the piezo-ceramic required for vibration stimulation being attached, in particular glued, to the underside of the disc facing away from the mesh membrane.

In an alternative embodiment of the present invention, the support structure is an annular piezoceramic. This achieves a greater vibration amplitude and thus greater energy, which is advantageous for the nebulization rate and the droplet size distribution. Furthermore, a production step can be saved, since the fastening, in particular gluing, of the piezoceramic on a steel disc can be omitted.

An epoxy resin is preferably used as the adhesive for attaching all parts of the aerosol generator according to the invention. This is easy to use, medically compatible, can be easily adjusted to the desired viscosity—firm enough not to flow away between application and pressing of the mesh membrane but liquid enough to easily penetrate the bonding openings—and cures quite quickly.

Further properties, features and advantages of the present invention are apparent from the exemplary embodiments explained in more detail below with reference to the figures. These are only intended to illustrate the present invention and are not intended to limit it in any way.

BRIEF DESCRIPTION OF THE DRAWINGS

It is shown in:

FIG. 1 shows a cross section through a possible embodiment of an aerosol generator according to the invention.

DETAILED DESCRIPTION OF ILLUSTRATIVE EMBODIMENTS

Figure 1:
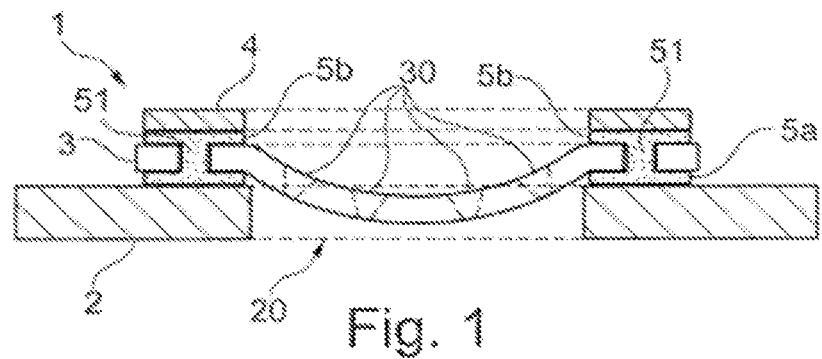
FIG. 1: A cross section through an embodiment of an aerosol generator according to the invention

The mesh membrane 3 is placed on the upper side of the support structure 2 and the closing ring 4 is in turn placed above it. The mesh membrane 3, which as shown has a flat, circular edge area and a convexly curved central area with funnel-shaped pores, has, in the flat outer area, a plurality of circumferentially arranged gluing openings that go through from the top to the bottom and are each filled by column-like structures 51 made of cured adhesive. The adhesive columns 51 connect a lower adhesive layer 5a to an upper adhesive layer 5b and thus form an adhesive structure which looks like an H lying on its side in cross-section. The adhesive layers 5a, 5b are bonded to the adjacent components made of a material suitable for bonding, namely the carrier structure 2 in the case of the lower adhesive layer 5a and the closing ring 4 in the case of the upper adhesive layer 5b. In order to guarantee the most harmonious possible vibration behavior of the aerosol generator, the adhesive layers have as uniform a thickness as possible. For the same reason, excess adhesive portions that have protruded laterally over the outer ring 4 or the mesh membrane 3 are preferably removed during the production according to the invention.

Figure 2:
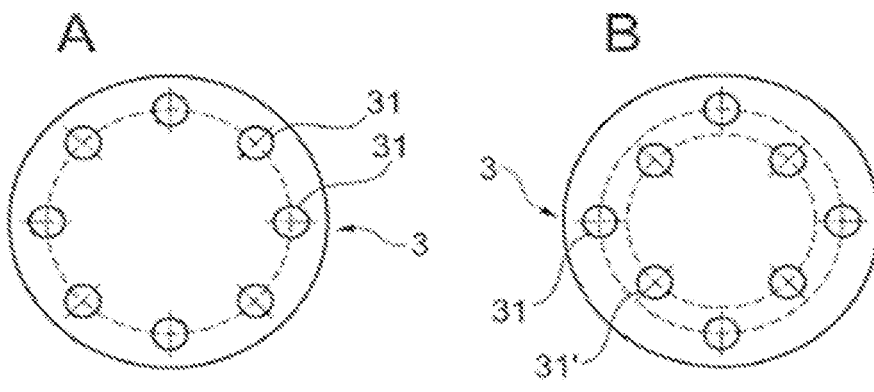
FIG. 2: Two possible embodiments of a mesh membrane of an aerosol generator according to the invention in a plan view

In two partial figures, FIG. 2 shows two possible embodiments of the mesh membrane of the aerosol generator according to the invention in a plan view.

Partial figure A shows a version with eight round gluing openings 31, which are distributed evenly, i.e. have an angular distance of 45 degrees between adjacent openings 31, around the circumference over the outer area of the mesh membrane 3, which is flat for surface contact on the carrier structure and has a circular outline. The gluing openings in this possible embodiment therefore lie on a concentric circle around the center point of the mesh membrane 3 and taken together form a regular octagon. The specific number of gluing openings has no meaning and is only for illustration. A higher or lower number would be equally conceivable as long as there are at least two or more, preferably three or more, gluing openings. The circular cross-section of the gluing openings shown here also only has a technical advantage insofar as such openings can be easily produced, for example by drilling, and can therefore also be subsequently inserted into a mesh membrane produced in a different way. However, if mesh membranes produced by means of casting or electro-galvanic deposition methods are used, gluing openings with other cross-sections, for example square, polygonal or in the shape of a segment of a circular ring, could equally be used.

Subfigure B shows an embodiment with gluing openings 31 arranged on two concentric rings around the center point of the mesh membrane 3, four gluing openings 31 being located on each of the two rings. The openings within a ring are angularly spaced 90 degrees between neighbors, and the openings of the two rings are offset by 45 degrees from each other.

The mechanical coupling properties of the mesh membrane to the carrier structure and thus the vibration properties and the shape of the standing wave that forms during vibration can be influenced by different combinations of ring radii and the number of gluing openings per ring. As a result, the droplet size distribution can be set as desired within a certain range and optimized with regard to the highest possible proportion of droplets that can enter the pulmonary alveoli (i.e. less than 5 micrometres).

Figure 3:
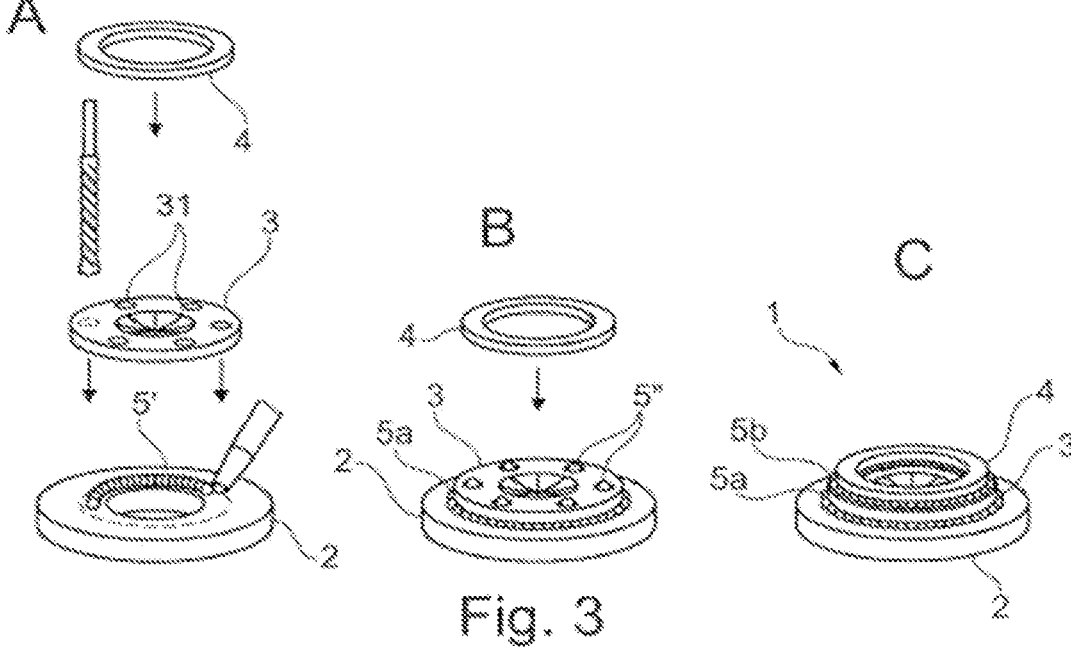
FIG. 3: An illustration of the manufacture of an aerosol generator according to the invention in three partial figures

FIG. 3 illustrates the production of an aerosol generator according to the invention in three subfigures.

Subfigure A illustrates the steps a) to c) of the manufacturing method according to the invention, i.e. the provision of the components, the carrier structure 2 comprising the piezoceramic, the mesh membrane 3 and the closing ring 4, the introduction of the circumferential gluing openings 31 (indicated by a drill bit) and the application of an annular formation of liquid adhesive 5' on the upper side of the carrier structure 2, the volume of the adhesive being dimensioned such that it is at least the volume of all gluing openings plus the volume of two layers of adhesive, taking into account any volume change during curing the two layers of adhesive and any losses.

Subfigure B shows production step d) of the method according to the invention, in which the mesh membrane 3 is placed with its flat outer area on the carrier structure 2 having the adhesive 5' on it and is pressed on in such a way that the viscous adhesive forms between carrier structure 2 and mesh membrane 3 an adhesive layer 5a as uniformly thick as possible and is pressed into and through the gluing openings 31 and finally forms adhesive spots 5'' protruding from the openings 31 over the upper side of the mesh membrane 3.

Subfigure C shows the last two production steps, e) and f). In step e), the closing ring 4 is first placed on the upper side of the mesh membrane 3 and the adhesive dots 5' protruding above it, positioned as desired and then pressed on in such a way that an adhesive layer 5b of the desired thickness is formed as evenly as possible between the mesh membrane 3 and the closing ring 4. In step f) the adhesive is now allowed to harden, which completes the production of the aerosol generator according to the invention.

LIST OF REFERENCE NUMERALS

1 aerosol generator
2 carrier structure/disc
20 opening
3 mesh membrane
31 gluing opening 4 closing ring
5a lower adhesive layer
5b upper adhesive layer
5' 5" liquid adhesive Although the embodiments of the present disclosure have been described with reference to preferred embodiments, workers skilled in the art will recognize that changes may be made in form and detail without departing from the spirit and scope of the present disclosure.

The invention claimed is:

1. An aerosol generator for use in a nebulizer for aerosolization of a fluid comprising:
   a carrier structure having a concentric, continuous opening;
   a mesh membrane covering the opening and overlaying an upper surface of the carrier structure;
   a closing ring arranged on an upper surface of the mesh membrane that faces away from the carrier structure, wherein:
   the mesh membrane includes at least two gluing openings extending from the upper surface of the mesh membrane to a lower surface of the mesh membrane that faces the carrier structure and distributed evenly around a circumference of the mesh membrane, and cured adhesive columns protruding through the gluing openings;
   the adhesive columns mechanically connect a lower adhesive layer that lies below the lower surface of the mesh membrane and is bonded to the upper surface of the carrier structure facing the mesh membrane with an upper adhesive layer that lies above the upper surface of the mesh membrane and is bonded to a lower surface of the closing ring facing the mesh membrane;
   the adhesive columns mechanically connect the mesh membrane to the carrier structure and the closing ring; and
   wherein the mesh membrane is not adhesively bonded across its entire surface to either the upper or lower adhesive layer or the adhesive columns, and an introduction of a force from a piezo ceramic into the mesh membrane is affected exclusively via the adhesive columns protruding through the gluing openings.

2. The aerosol generator according to claim 1, wherein the mesh membrane is made of a material that is not bondable by means of an adhesive approved for contact with active ingredient solutions.

3. The aerosol generator according to claim 2, wherein the mesh membrane is made of nickel or a fluorine-containing plastic.

4. The aerosol generator according to claim 1, wherein the at least two gluing openings in the mesh membrane comprise three or more gluing openings in the mesh membrane.

5. The aerosol generator according to claim 1, wherein the mesh membrane has a circular outline.

6. The aerosol generator according to claim 1, wherein the at least two gluing openings are arranged on exactly one circle or on exactly two circles around a center point of the opening of the carrier structure.

7. The aerosol generator according to claim 1, wherein the carrier structure comprises a steel disk having an annular piezo ceramic attached on its lower surface facing away from the mesh membrane.

8. The aerosol generator according to claim 1, wherein the carrier structure comprises an annular piezo ceramic.

9. The aerosol generator according to claim 1, wherein the at least two gluing openings are round and a distance from a center of each gluing opening to an edge of the mesh membrane is not less than one and a half times a radius of the gluing openings.

10. The aerosol generator according to claim 1, wherein the adhesive columns and adhesive layers comprise an epoxy resin based adhesive.

11. A method of manufacturing an aerosol generator comprising:
   providing a mesh membrane, an annular closing ring having an opening and an annular carrier structure having and opening that is concentric to the opening of the annular closing ring,
   introducing at least two gluing openings spaced evenly along a circumference of the mesh membrane in a desired pattern;
   applying, on an upper surface of the carrier structure, a ring of adhesive, which encloses the opening, wherein a total adhesive volume of the ring of adhesive is dimensioned larger than the total volume of all the gluing openings of the mesh membrane;
   placing the mesh membrane over the ring of adhesive and the carrier structure and pressing the mesh membrane toward the upper surface of the carrier structure, wherein the ring of adhesive is pressed and forms a lower adhesive layer between the carrier structure and the mesh membrane, and extends through the gluing openings and forms adhesive dots protruding above an upper surface of the mesh membrane facing away from the carrier structure;
   placing and pressing the closing ring toward the upper surface of the mesh structure, wherein an upper adhesive layer is formed between the mesh membrane and the closing ring; and
   allowing the adhesive to cure,
   wherein the mesh membrane is not adhesively bonded across its entire surface to either the upper or lower adhesive layer, and the introduction of a force from a piezo ceramic into the mesh membrane is effected exclusively via the adhesive columns protruding through the gluing openings.

12. The method according to claim 11, further comprising, after allowing the adhesive to cure, removing protruding adhesive residue.

* * * * *